United States Patent [19]

Jordan et al.

[11] Patent Number: 4,793,218

[45] Date of Patent: Dec. 27, 1988

[54] METHOD OF FORMING KNIFE BLADES BY PHOTO-CHEMICAL ETCHING

[76] Inventors: George Jordan, 2620 Temple Heights Dr., Oceanside, Calif. 92056; Dimitri G. Mondiadis, 28 Sylvan St., Melrose, Mass. 02176

[21] Appl. No.: 106,383

[22] Filed: Oct. 9, 1987

[51] Int. Cl.⁴ .............................................. B21D 35/00
[52] U.S. Cl. .................................... 76/101 R; 430/320
[58] Field of Search ....... 76/101 R, 101 SM, DIG. 8; 430/320, 269

[56] References Cited

U.S. PATENT DOCUMENTS

| | | | |
|---|---|---|---|
| 3,696,013 | 10/1972 | Tafapolsky | 204/231 |
| 3,916,749 | 11/1975 | Armelin | 76/101 A |
| 4,587,202 | 5/1986 | Borysko | 430/320 |
| 4,713,315 | 12/1987 | Smith | 430/320 |

*Primary Examiner*—Roscoe V. Parker
*Attorney, Agent, or Firm*—Peter L. Berger

[57] ABSTRACT

A method of forming knife blades from a flat section of pre-hardened metal such that each blade has a predetermined shape, includes the steps of photo-chemically etching a plurality of blanks from the section of metal so that each blank has a respective predetermined shape; and sharpening at least one edge of each blank by grinding the at least one edge.

9 Claims, 1 Drawing Sheet

U.S. Patent  Dec. 27, 1988  4,793,218
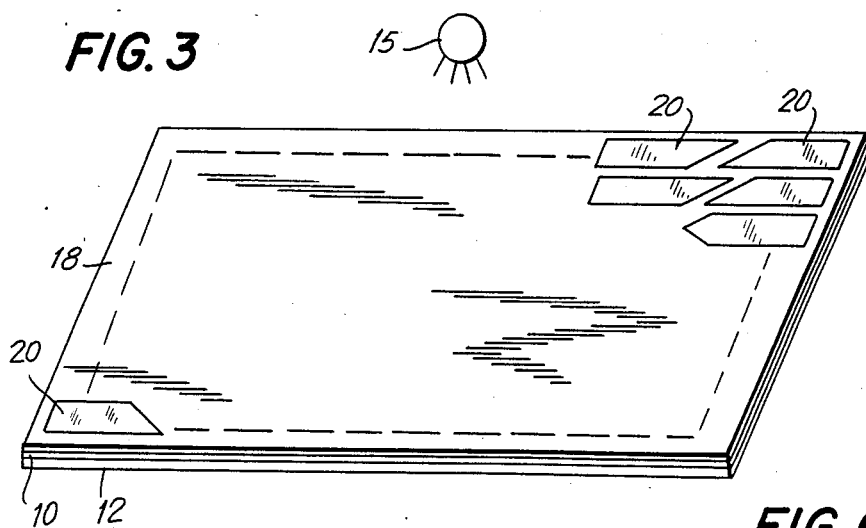
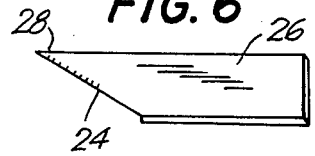
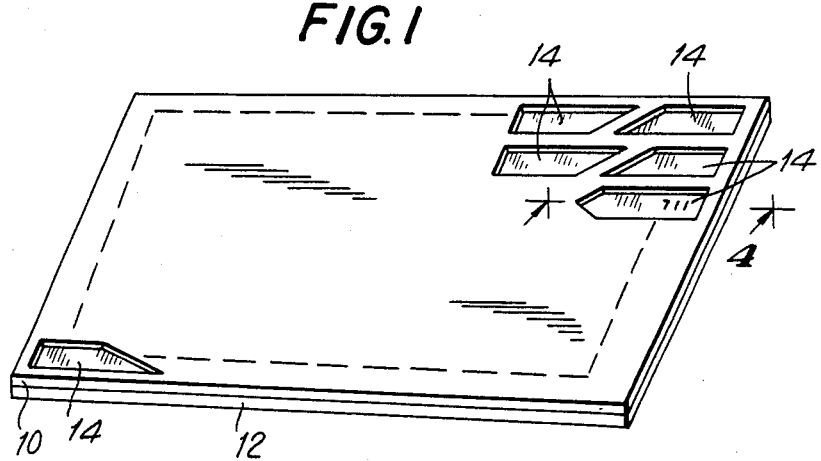
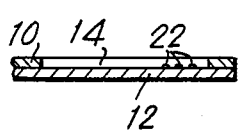
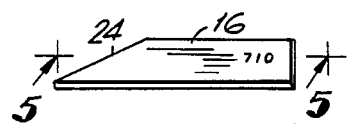
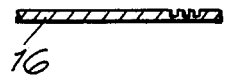

METHOD OF FORMING KNIFE BLADES BY PHOTO-CHEMICAL ETCHING

BACKGROUND OF THE INVENTION

This invention relates generally to knife blades, and more particularly, is directed to the formation of surgical knife blades.

In order to produce surgical blades, for example, for microsurgery and special surgery such as eye, ENT (ear, nose and throat), neurological, vascular, OB/GYN and the like, blanks having the desired shape of the blade are first cut from a section of soft flat stock of stainless steel or the like in a variety of thicknesses on the order of 0.0015 inch to 0.095 inch. This has conventionally been performed by forging dies, or use of male and female cutting dies, or alternatively, by a wire EDM method which uses an electrical discharge to burn through the material. This, of course, in the case of the cutting dies, requires specially designed and expensive tooling, such as perforating dies, stamping dies or forging dies, in addition to other equipment. In practice, a single or a plurality of blanks are cut simultaneously from the same section of flat stock. Then, the blanks are sequentially straightened, hardened, tempered and tumbled to remove burrs and discoloration, sharpened by grinding and then buffed to smooth the ground edge. As to the grinding step, a variety of grinding wheels are used, such as a 38A grade A10 wheel sold by Norton.

This process, however, has various disadvantages. First, because the blanks are either die cut or electrically cut from the flat stock, the shapes of the blanks may not be as precise as desired. Related thereto, the blanks that are produced by the aforementioned dies are inherently not flat. This is because the dies push through the metal with a force. Thus, as a result, mechanical stresses are also introduced into the blank material. Further, the blanks are formed with burrs which must be removed. Accordingly, the aforementioned additional step of tumbling is required. However, since the blanks must have certain critical tolerances of for example ±0.003 inch, this blanking step is not very precise.

In addition, when cutting the blanks in accordance with the aforementioned known processes, soft or semi-hard stainless steels are commonly used, since the dies or electrical discharge will not satisfactorily and efficiently cut through a hard stainless steel. As a result, it may be necessary to straighten the blanks after they are cut. Further, the blanks must be tempered to achieve alignment of the metal grain structure, which is necessary to achieve proper hardness for the later sharpening operation. This is performed by the rolling and heat treating steps discussed above, prior to the tumbling step.

Because the heat-treated and tempered blanks have a discoloration due to oxidation, they must be treated in specially designed ovens and furnaces with individually suited atmospheric or vacuum conditions. As such, the blanks are chemically treated to minimize such oxidation and discoloration. The blanks are then chemically or mechanically cleaned.

Further, because the dies occupy space, sufficient room must be provided between blanks to be cut to accommodate the dies. This, of course, results in a waste of material in the flat stock.

It may also be desirable to place markings on the knife blades, such as a logo or the like. With the aforementioned methods of forming knife blades, an additional die is necessary to mechanically insert the logo in the knife blades. In addition to adding to the costs, this additional step may also slightly distort the knife blades and add additional stresses therein, which may result in breaking of the blades. Further, the markings are sometimes distorted to some extent due to mechanical warping.

It will be appreciated that the above known methods require expensive capital equipment, and each of the steps must be carefully monitored for hardness, finish, and the like.

Of interest to the present invention are U.S. Pat. Nos. 3,916,749 and 3,696,013.

OBJECTS AND SUMMARY OF THE INVENTION

Accordingly, it is an object of the present invention to provide a method of forming knife blades that overcomes the aforementioned problems.

It is another object of the present invention to provide a method of forming knife blades by photo-chemical etching.

It is still another object of the present invention to provide a method of forming knife blades from blanks photo-chemically etched from flat stock of hardened stainless steel.

It is yet another object of the present invention to provide a method of forming knife blades from blanks that does not require any rolling, heat treating or tumbling of the blanks.

It is a further object of the present invention to provide a method of forming knife blades from blanks photo-chemically etched from flat stock of hard stainless steel or other materials such as ceramics, synthetic gems, other metals and the like.

It is a still further object of the present invention to provide a method of forming knife blades that is material efficient so as to maximize the use of the material of a section of flat stock used to form blanks for the knife blades.

It is a yet further object of the present invention to provide a method of forming knife blades in which the knife blades can have markings placed thereon when the blanks are initially formed on one or both sides without inducing stresses.

It is another object of the present invention to provide a method of forming knife blades that is economical and easy to use.

In accordance with an aspect of the present invention, a method of forming knife blades from a flat section of pre-hardened metal such that each blade has a predetermined shape, includes the steps of photo-chemically etching a plurality of blanks from the section of pre-hardened metal so that each blank has a respective predetermined and precise shape; and sharpening at least one edge of each blank by grinding the at least one edge.

The above and other objects, features and advantages of the present invention will become readily apparent from the following detailed description which is to be read in connection with the accompanying drawings.

BRIEF DESCRIPTION OF THE DRAWINGS

FIG. 1 is a perspective view showing a flat section of stainless steel covered with a photo-chemical etchant in selected areas according to a first embodiment of the present invention;

FIG. 2 is a perspective view of a knife blank formed from the stainless steel section of FIG. 1;

FIG. 3 is a perspective view showing a flat section of stainless steel having its entire surface covered with a photo-chemical etchant and then covered by a transparency containing light blocking areas in selected areas according to a second embodiment of the present invention;

FIG. 4 is a cross-sectional view taken along line 4—4 of FIG. 1;

FIG. 5 is a cross-sectional view taken along line 5—5 FIG. 2; and

FIG. 6 is a perspective view of a knife blade formed according to the present invention.

DETAILED DESCRIPTION OF THE PREFERRED EMBODIMENTS

Referring to the drawings in detail, in accordance with the present invention, a section of thin, pre-hardened and polished flat stock of stainless steel is photo-chemically etched to produce a plurality of knife blades. The art of photo-chemically etching is old and need not be explained in detail herein, although a few brief examples will now be given.

As a first example, as shown in FIG. I, an optically activated chemical etchant 10 which is well known can be screen printed on the surface of the section of flat stock 12 of pre-hardened stainless steel in accordance with a desired pattern of knife blades to be formed. The thin flat stock 12 of stainless steel preferably has a thickness in the range from 0.0015 inch to 0.095 inch, and a hardness in the range of 53 to 58 on the Rockwell C hardness scale, which exhibits an excellent grain structure most suitable for razor sharp edges having excellent edge attrition qualities. Specifically, the chemical etchant 10 is screen printed or photographically deposited on the entire surface of the stainless steel stock 12 except in those areas 14 from which the knife blades are to be formed. In this regard, areas 14 have a predetermined shape which correspond identically to the knife blanks to be formed from stainless steel stock 12. Then, the chemical etchant 10 is exposed to light from a light source 15 which activates the chemical etchant 10 to etch away and dissolve the stainless steel surrounding such areas 14, leaving a plurality of knife blanks 16 remaining, one of which is shown in FIG. 2.

Alternatively, as shown in FIG. 8, chemical etchant 10 can be spread on the entire surface of the section 12 of flat stock, and a transparency 18 containing the desired pattern positioned thereover, that is, with transparency 18 including light blocking areas 20 corresponding to areas 14 of FIG. 1 where the knife blanks 16 are to be formed. Then, light from light source 15 is projected through transparency 18 onto the surface of stainless steel stock 12. As a result, chemical etchant 12 is activated to etch away and dissolve the stainless steel 10 in all areas except the light blocking areas 20, whereupon knife blanks 16 are once again formed.

The aforementioned photo-chemical etching techniques can be performed in a conventional manner, for example, as performed by the photofabrication industry. The photo-chemical etchant 10 can be any well known material which is conventionally used for etching, such as a metal containing material like a metal oxide. For example, photo-chemical etching is discussed in detail in an article by the Department of Defense, Information Analysis Center, Machinability Data Center, entitled "Chemical Machining Production With Chemistry", DOD Publication No. MDC77-102, 1977, and in the book "The Principles and Practice of Photochemical Machining and Photo-etching" by D. M. Allen, published by Adam Hilger, 1986.

It will be appreciated from the above that surrounded areas 14 and light blocking areas 20 can be positioned extremely close to each other, which could not occur with the aforementioned prior art dies and wire EDM method. As a result, there is maximum usage of the section 12 of flat stock, that is, there is little waste of the stainless steel material, resulting in a savings of approximately 20% of the stainless steel material. Further, because the blanks 16 are not mechanically punched out or electrically burned out, a hardened stainless steel material can be used for the section 12 of flat stock. Thus, the steps of rolling, hardening, tempering and polishing (tumbling) can be performed on the large sheets of stainless steel at the steel mill on large, very precise equipment. In other words, these latter steps can be eliminated after the knife blanks 16 are formed. As a result, approximately 45% of the costs for forming the knife blades according to the prior art can be eliminated. Further, tooling up costs according to the present invention are about $500.00 per shape as opposed to $8,500.00 to $8,000 00 or more per shape according to the prior art dies. Also, there is greater flexibility as to design changes with the present invention, and tooling up can be performed quicker, that is, in three to four weeks.

Still further, because of the photo-chemical etchant 10, knife blanks 16 are formed with very precise shapes which are identical to the predetermined shapes of the surrounded areas 14 and light blocking area ®20. Thus, the method according to the present invention has an accuracy of approximately 0.001 inch or better, and there are no burrs to be removed. Also, because there is no mechanical cutting as with the aforementioned dies, there are no additional stresses introduced into the knife blanks 16. In other words, the knife blanks are formed flat without warp or bow, allowing more precise grinding. Also, because of the precise shape of the knife blades, they can be formed so as to easily attach to a handle. In this regard, the knife blades can be formed with special assymetric shapes and/or screw threads or the like so that each blade can be easily secured to a handle.

Lastly, in order to etch a logo or other markings into knife blanks 16, it is only necessary to slightly vary the areas in which the etchant 10 is deposited on the surface of the stainless steel stock 12. For example, as shown in FIGS. 1, 2 and 4, if it is desired to etch the numbers "711" into the surface of a knife blank 16, a small amount 22 of etchant is placed in an area 14, with the pattern "711". Then, when the etchant 22 is exposed to light, it will burn only partially through the stainless steel material, as shown in FIG. 5. There is thus no need to provide an additional step to imprint the markings, as is conventional in the prior art after the knife blade is formed. Further, the stresses induced by such additional imprinting step according to the prior art are eliminated.

Further, the blanks can be formed with depressions, threads or the like for attaching the same to a handle in the same photo-chemical etching process.

After the knife blanks 16 are formed, at least one edge 24 thereof is sharpened with a grinding wheel in a conventional manner to form the sharpened knife blades 26, as shown in FIG. 6.

In some cases, it is desirable to place markings on the blades for depth gauging in certain microsurgical procedures, in increments for example of up to 0.0001 inch without degrading the cutting edge efficacy. This can be performed in the same manner as the markings discussed above on blanks 16, to form additional gauge markings 28, shown in FIG. 6.

Having described specific preferred embodiments of the invention with reference to the accompanying drawings, it will be appreciated that the present invention is not limited to those precise embodiments, and that various changes and modifications may be effected therein by one of ordinary skill in the art without departing from the scope or spirit of the invention as defined in the appended claims.

What is claimed is:

1. A method of forming knife blades from a flat section of pre-hardened metal such that each blade has a predetermined shape, comprising the steps of:
   photo-chemically etching a plurality of blanks from said flat section of pre-hardened metal so that each said blank has a respective predetermined shape; and
   sharpening at least one edge of each blank by grinding said at least one edge.

2. A method according to claim 1; wherein said step of sharpening includes the step of grinding said at least one edge by a rotating grinding wheel.

3. A method according to claim 1; wherein said predetermined shape facilitates securing each said knife blade to a handle.

4. A method according to claim 3; wherein said predetermined shape includes an assymetric shape or screw threads.

5. A method according to claim 1; wherein said flat section of metal is a section of flat stock of pre-hardened and pre-rolled stainless steel.

6. A method according to claim 1; wherein said step of photo-chemically etching includes the steps of:
   covering an entire surface of said flat section of metal with a photo-chemical etchant;
   placing a transparency having light blocking areas which define the knife blanks to be formed, over said covered surface; and
   exposing said transparency to light such that said photo-chemical etchant etches away all of said flat section except in portions thereof covered by said light blocking areas.

7. A method according to claim 6; wherein said photo-chemical etchant is a metal containing compound.

8. A method according to claim 1; wherein said step of photo-chemically etching includes the steps of:
   covering an entire surface of said flat section of metal with a photo-chemical etchant except in predetermined areas corresponding to said predetermined shapes;
   exposing said covered surface to light such that said photo-chemical etchant etches away said flat section only in areas thereof covered by said etchant.

9. A method according to claim 8; wherein said photo-chemical etchant is a metal containing compound.

* * * * *